(12) United States Patent
Luzbetak et al.

(10) Patent No.: US 7,824,361 B2
(45) Date of Patent: Nov. 2, 2010

(54) CONNECTOR FOR USE IN SINGLE AND DOUBLE BREAST PUMPING

(75) Inventors: Mark A. Luzbetak, Kildeer, IL (US); Thomas A. Sutrina, Rockford, IL (US)

(73) Assignee: Medela Holding AG, Baar (CH)

( * ) Notice: Subject to any disclaimer, the term of this patent is extended or adjusted under 35 U.S.C. 154(b) by 604 days.

(21) Appl. No.: 11/580,465

(22) Filed: Oct. 13, 2006

(65) Prior Publication Data

US 2008/0090444 A1    Apr. 17, 2008

(51) Int. Cl.
*A61M 1/06*    (2006.01)

(52) U.S. Cl. ........................................... 604/74

(58) Field of Classification Search ............ 604/74, 604/131, 176, 19, 76, 533–534; 285/127.2, 285/129.1, 130.1, 131.1, 133.21, 133.3, 125.1; 403/170; 128/205.24
See application file for complete search history.

(56) References Cited

U.S. PATENT DOCUMENTS

| | | | | |
|---|---|---|---|---|
| 1,030,107 A | * | 6/1912 | McCormick | 285/130.1 |
| 2,534,577 A | | 12/1950 | Courtot | |
| 3,991,762 A | * | 11/1976 | Radford | 604/119 |
| 4,489,721 A | * | 12/1984 | Ozaki et al. | 128/205.24 |
| 4,674,496 A | * | 6/1987 | Svadjian et al. | 128/207.16 |
| 4,718,453 A | | 1/1988 | Ahrens | |
| 5,163,902 A | * | 11/1992 | Lynn et al. | 604/86 |
| 5,201,860 A | * | 4/1993 | Richardson | 47/39 |
| 5,333,606 A | * | 8/1994 | Schneider et al. | 128/200.24 |
| 5,392,772 A | * | 2/1995 | Zilbershtein | 128/205.24 |
| 5,441,080 A | | 8/1995 | Baumann | |
| 5,705,737 A | * | 1/1998 | Liao | 73/49.7 |
| 5,711,294 A | * | 1/1998 | Kee et al. | 128/202.27 |
| 5,720,722 A | | 2/1998 | Lockridge | |
| 5,944,441 A | * | 8/1999 | Schutze | 403/403 |
| 6,070,915 A | * | 6/2000 | Luo | 285/125.1 |
| 6,609,515 B2 | * | 8/2003 | Bienvenu et al. | 128/200.21 |
| 6,675,834 B1 | * | 1/2004 | Lai | 137/625.47 |
| 2004/0127845 A1 | | 7/2004 | Renz et al. | |
| 2005/0033267 A1 | * | 2/2005 | Decaria | 604/533 |

\* cited by examiner

*Primary Examiner*—Nicholas D Lucchesi
*Assistant Examiner*—Diva Ranade
(74) *Attorney, Agent, or Firm*—McDonnell Boehnen Hulbert & Berghoff LLP

(57) ABSTRACT

The connector of the present invention provides fewer connections and attachments to a breastpump configured for expressing breast milk from both of a woman's breasts simultaneously, thereby facilitating easier use of the breast pump and yielding fewer pieces for the user to carry or misplace. The connector includes a manifold with four ports. Individual tubes extend from three of the four ports and each has a plug member. One tube engages with a vacuum source and the remaining two tubes engage with a breastshield assembly for double breast pumping. When single breastpumping is desired, one of the two tubes connected to the breastpump assemblies is disconnected and engaged with the dock port of the manifold.

15 Claims, 4 Drawing Sheets

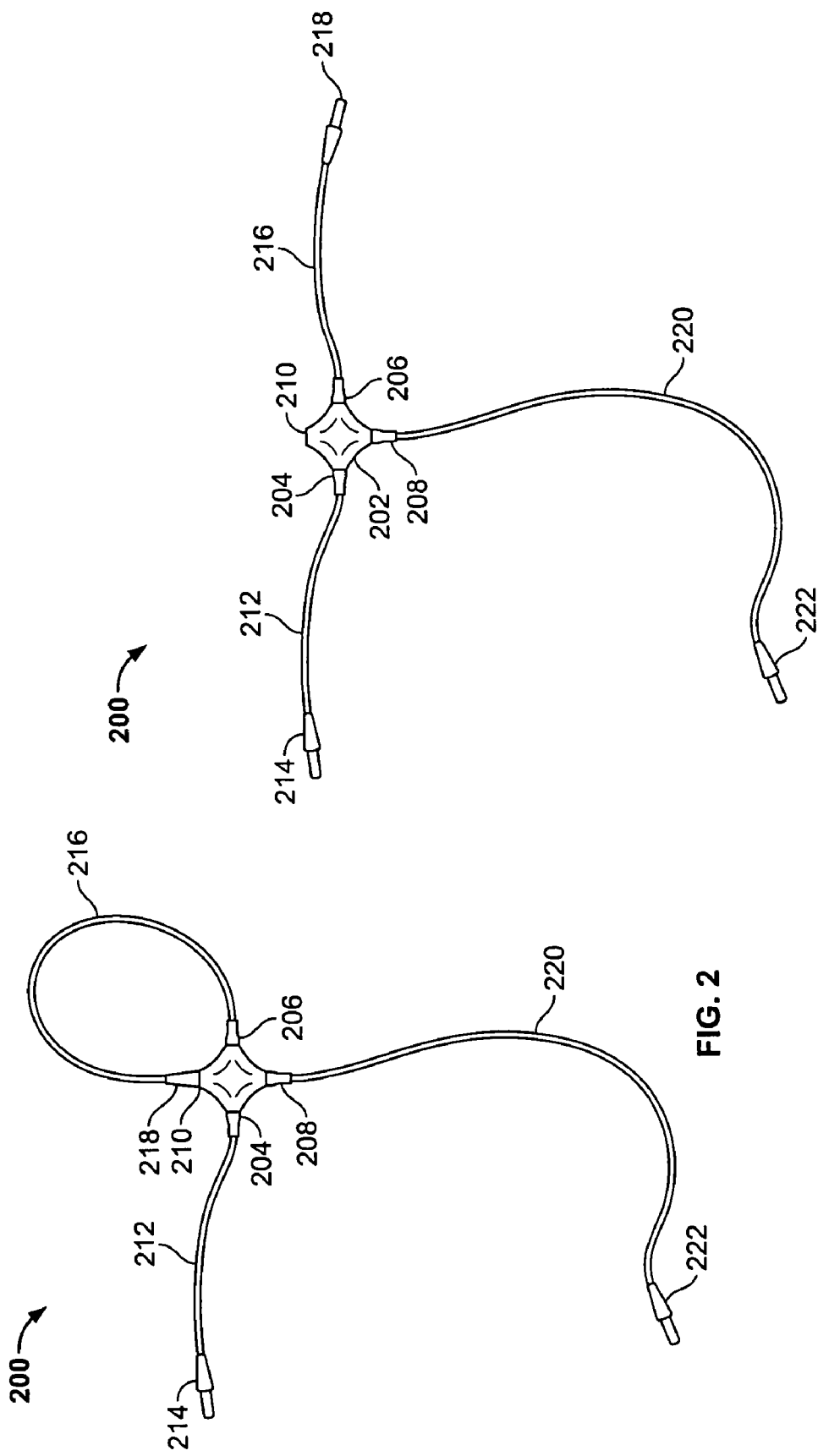

CONNECTOR FOR USE IN SINGLE AND DOUBLE BREAST PUMPING

FIELD OF THE INVENTION

The present invention relates to breastpumps, and more specifically to a breastpump system or assembly which can be used in both single and double pumping modes of operation. In particular, the invention includes a connector, which permits a variety of configurations to enable use of a breastpump in either single or double pumping modes.

BACKGROUND OF THE INVENTION

Breastmilk pumps are well-known, and generally comprise a hood, or shield, which fits over the breast. A vacuum pump is connected to the shield for generating an intermittent vacuum (i.e., negative pressure) within the shield. A receptacle is provided in communication with the shield for receiving the breast milk expressed during operation of the pump.

The action of the pump creates an intermittent vacuum within the shield, which serves to create an environment reminiscent of suckling and thus, causes expression of breast milk from the mother's breast. The milk so expressed is ordinarily collected in a bottle or other container for storage and later use. Such breast pumps are disclosed in U.S. Pat. Nos. 4,857,051; 5,007,899; and 5,071,403 for example.

It is also well-known to provide a breast pump which can be used in both single (one breast) and double (both breasts) modes of operation, i.e., expressing breast milk from one breast at a time or simultaneously. For example, Medela, Inc., to which the present invention is assigned, provides a multi-port connector for use with its commercialized CLASSIC vacuum pump apparatus. In a double-pumping mode, two airlines connect to a pair of ports in a connector, which in turn is connected to a pump. The airlines are individually connected to two breast pump assemblies (to convey changes in pressure to the connected breast shields). Two adapters are further provided, each containing a milk barrier to prevent milk from reaching the vacuum pump. Each adapter is releasably attached to a respective breast pump assembly through a threaded engagement. This arrangement using the connector including two adapters of the foregoing type is disclosed in U.S. Pat. No. 5,071,403.

With the above noted configuration, single pumping is achieved by removing one of the tubes from the connector to disconnect the breastshield. A plug is inserted into the joint or receptacle from which the tube was removed so that suction is achieved only in the remaining breastshield. In using this design, the user has to disconnect the tube from both the shield and the joint and plug the joint to inactivate one of the two breast shields. The suction level for single pumping can be higher due to the loss in fluid volume compared with two breast shields. The removed tubing can be misplaced or lost.

U.S. Pat. No. 5,720,722 is a connector for use in single and double breast pumping. This connector has a tubular housing with an internal wall extending across the housing interior to divide it into two chambers. One chamber has an outlet for attachment to an air tube for single breast pumping, while the second chamber has two outlets for attachment to two air tubes for double breast pumping.

In this configuration, when a woman wants to only pump one breast, the tube from the inactive breastshield is removed from the breast pump and a plug is inserted into the open port of the pump to close it off. The plug may also provide for a predetermined amount of air leakage to simulate the load of the disconnected breastshield, so that the single shield pumping suction level is substantially the same to the double pumping vacuum level. However, the user may accidentally tangle the two tubes, either during storage, setup, or use. Tangled tubes can also lead to a nursing mother accidentally disconnecting the incorrect breastshield when single breast pumping is desired.

Thus, a breastpump that eliminates a significant number of connections and attachment parts for transition between single and double breast pumping would be considered a desired improvement in the art, thereby facilitating easier use of a breast pump and yielding fewer parts for the user to carry, clean, misplace or manipulate.

SUMMARY OF THE INVENTION

An aspect of the present invention eliminates a significant number of attachment parts, and the need for adapters, to provide a breast pump which uses fewer connections and attachments, thereby facilitating easier use of the breast pump and yielding fewer pieces for the user to carry, clean, misplace or manipulate.

A further objective is to provide a connector that is readily used in either a single or double pumping mode through an easy and effective engagement of a fluid conveying device.

An aspect of the invention provides a connector including a manifold. The manifold includes a three-way passageway formed therethrough. The manifold includes a first port, a second port, a third port and a fourth port. The first, second and third ports are in fluid communication with the three-way passageway. A first tube is connected to and in fluid communication with the first port. A second tube is connected to and in fluid communication with the second port and a third tube is connected to and in fluid communication with the third port. The third tube is sized and shaped to be connectable to a vacuum source, and the fourth port is sized and shaped to receive one of the first tube and the second tube and permit a predetermined amount of fluid to pass by way of a leakage path. The leakage path can be formed in the fourth port or in the manifold.

Other embodiments of the invention include a plug member that terminates each tube. The first tube terminates with a first plug member, the second tube terminates with a second plug member and the third tube terminates with a third plug member. The third plug member is sized and shaped to be connectable to a vacuum source and the fourth port is sized and shaped to receive one of the first plug member and the second plug member.

Another embodiment includes a plug member within the fourth port of the manifold. One of the first tube or second tube is adapted to connect to the plug member of the fourth port.

Other embodiments of the invention provide the first, second and third tubes non-removably connected to the manifold. The fourth port may include an O-ring disposed therein, the O-ring including a pathway formed thereon for permitting air to be drawn therepast. The three-way passageway may be a T-shaped or Y-shaped passageway formed in the manifold. The plug members may engage with a respective one of the ports in a substantially fluid tight fit.

Another embodiment of the invention provides a system for breastpumping in a single breastpumping mode or a double breastpumping mode, including a source of intermittent vacuum. First and second breast shields are connectable to the source of vacuum. A connector is provided which includes a connector body having four spaced ports, a first tube extending from a first of the four ports with a first tube end adapted to connect to the source of intermittent vacuum.

A second tube extends from a second of the four ports with a second tube end adapted to connect to one of the first and second breast shields. A third tube extends from a third of the four ports with a third tube end adapted to connect to the other of the first and second breast shields. A passageway is formed in a central body of the connector, the passageway fluidly connecting the first, second and third tubes, and a fourth of the four ports adapted to receive one of the second and third tube ends and functioning to substantially seal the received tube end.

Yet other embodiments of the invention provide the first, second and third tubes being non-removably connected to the connector body. The passageway may be a three-way passageway. The passageway may be a T-shaped or Y-shaped passageway. The fourth of the four ports may be substantially sealed and provided with a predetermined amount of leakage.

It will of course be understood that the aspects and objectives of the invention are various, and need not be all present in any given embodiment of the invention. The features, advantages and accomplishments of the invention will be further appreciated and understood upon consideration of the following detailed description of an embodiment of the invention, taken in conjunction with the drawings, in which:

BRIEF DESCRIPTION OF THE DRAWINGS

The foregoing objectives and advantages of the invention will be further understood upon consideration of the following detailed description of an embodiment of the invention taken in conjunction with the drawings, in which:

FIG. 2 is a perspective view of a connector according to one embodiment of the present invention in a single pumping configuration or mode;

FIG. 3 is a perspective view of the connector of FIG. 2 in a double pumping configuration or mode;

DETAILED DESCRIPTION OF AN EMBODIMENT OF THE INVENTION

The connector of the present invention will be described herein in use with a breastpump assembly, but it is contemplated that the connector of the present invention can be used in any device that may benefit from this type of connector.

Figure 1:
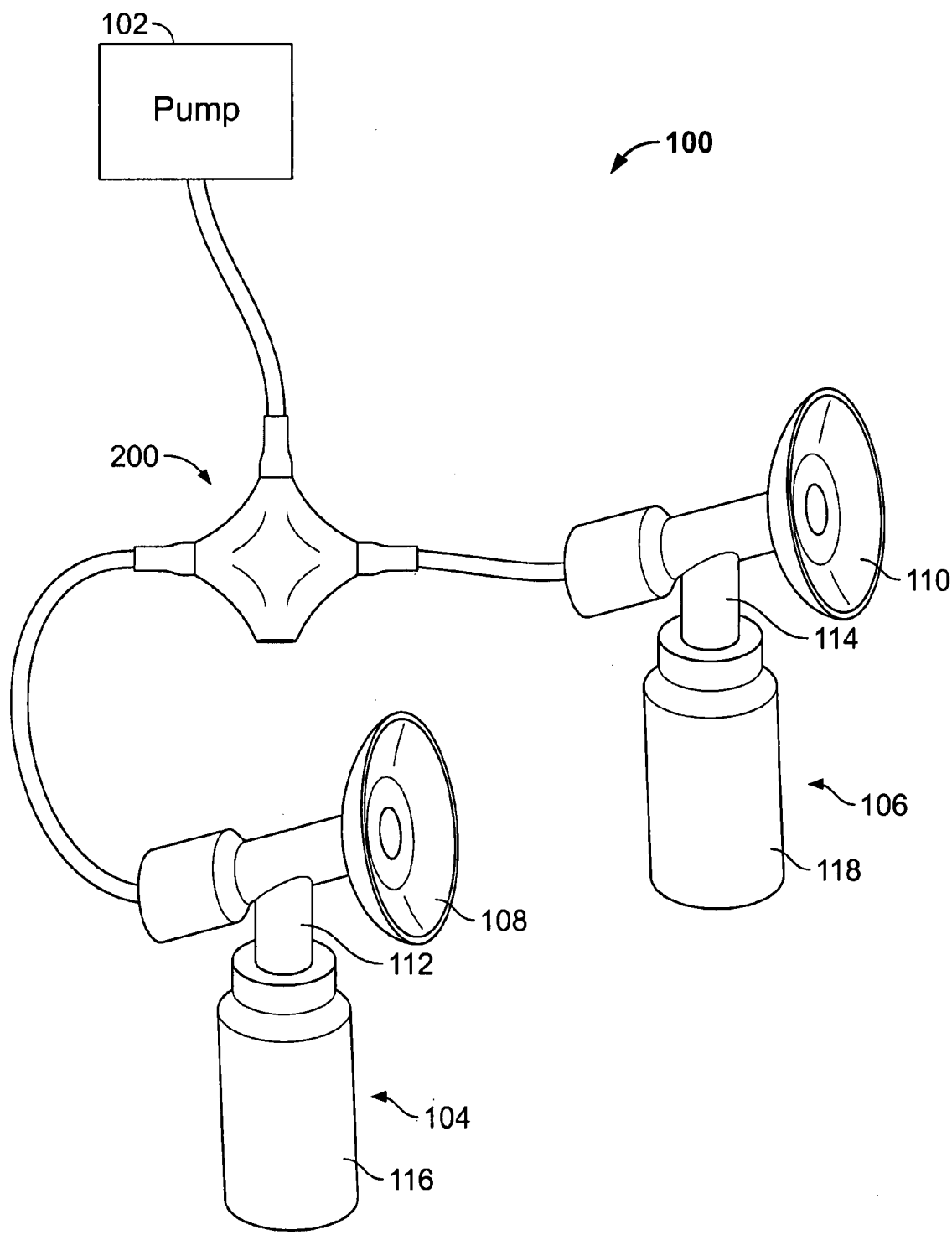
FIG. 1 is a diagrammatic drawing of a breast pump assembly incorporating a connector for use in single and double breast pumping according to one embodiment of the present invention.

A breastpump assembly 100 for pumping two breasts simultaneously or a single breast shows, in FIG. 1, a vacuum pump 102, which is used to generate a periodic change in pressure or intermittent vacuum. The generated change in pressure from the pump 102 is then transmitted through connector 200. The connector 20 may be configured to supply changes in pressure to breastshield assemblies 104, 106 simultaneously or only one of the two assemblies.

As referred to herein, vacuum is meant to denote a pressure less than ambient and in one configuration of the connector 200 is supplied to the breast shields 108, 110, and through the breast shields applied to a breast placed therein to express milk. Reference to a tube or passage hereafter as an "air" tube or a "vacuum" tube is not intended to be limiting.

The breast shield assemblies 104, 106 may each include, in addition to the shields 108, 110, a respective conduit structure 112, 114. Each respective conduit structure 112, 114, is typically provided in fluid communication with a collecting container, a bottle or the like, 116, 118.

FIGS. 2 and 3 illustrate a connector 200 according to the illustrated embodiment of the present invention in a single pumping and a double pumping configuration, respectively. The connector 200 includes a manifold 202. The manifold 202 is a central body including four spaced receptacles or ports, 204, 206, 208, and 210.

The connector 200 includes three tubes, a first tube 212, a second tube 216 and a third tube 220. A first tube 212 is connected to and extends from port 204 and may further include a first plug member 214 at a terminal end thereof. A second tube 216 is connected to and extends from port 206 and may further include a second plug member 218 at a terminal end thereof. A third tube 220 is connected to and extends from port 208 and may further include a third plug member 222 at a terminal end thereof. Tubes 212, 216, 220 are preferably permanently affixed within ports 204, 206, 208 such that tubes 212, 216, 220 are not detachable from the manifold, which is considered one advantage over the prior art.

The port or dock port 210 includes a tube connector arrangement (see FIG. 4), as disclosed and described in patent application Ser. No. 11/581,210 incorporated herein by reference. The port 210 permits connection and disconnection of either tube 214, 216 when single breast pumping is desired. More particularly, port 210 permits connection and disconnection of either of plug members 214, 218 when single breast pumping is desired.

Plug member 222, when engaged with an operating vacuum pump transmits changes in pressure from the pump to the manifold 202 and through tubes 212 and 216 to one or both of the breastpump assemblies. When single breast pumping is desired, one of either tube 212 or tube 216 is disconnected from the respective breastpump assembly and docked or engaged with port 210. The plug 214 or 218 (depending on which single breast a nursing mother wishes to pump) engages with the tube connector arrangement within dock port 210 and changes in pressure generated by the pump are conveyed through the manifold 202 to the tube not connected to dock port 210. Likewise, the dock port 210 can include a plug member such that either tube 212 or tube 216 can connect thereto.

Figure 4:
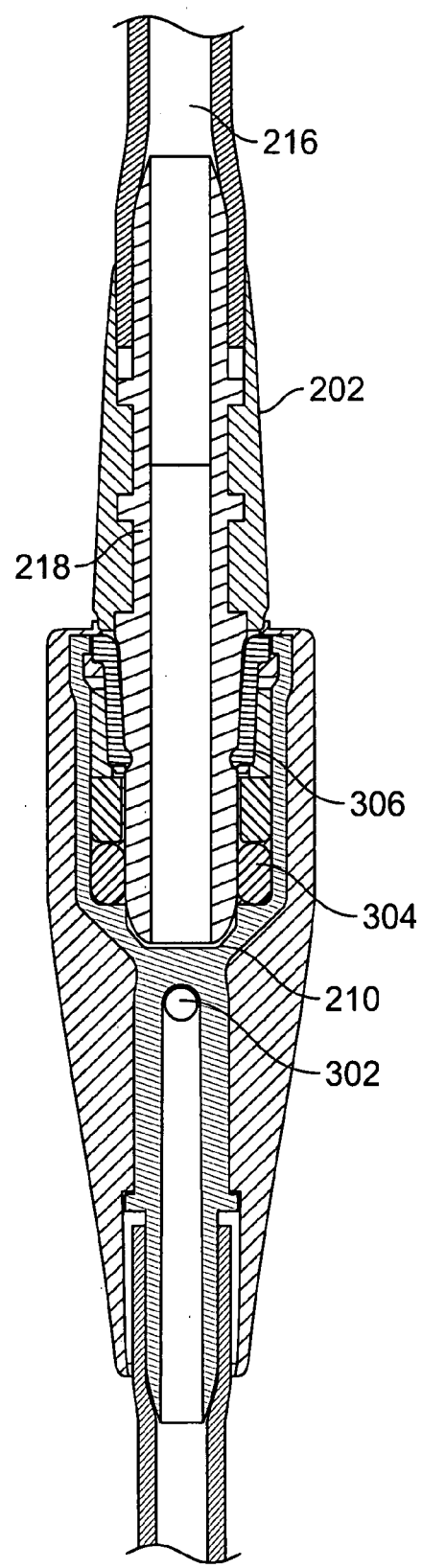
FIG. 4 is a cross-sectional view of a manifold and connected terminal fastener or plug for the connector according to one embodiment of the present invention.

As shown in the cross-sectional view of the manifold of FIG. 4, the tube connector arrangement within port 210 includes a sealing ring 304 and latching component 306, again fully described in patent application Ser. No. 11/581,210, for engagement with plug connector 214 or 218 (here, 218). The manifold 202 includes a three-way, or T-shaped or Y-shaped, flow passage 302 to convey the vacuum from the pump to the connector 200 and into separate air paths via tube 212 and/or 216 depending on whether single or double breast pumping is implemented. The passage 302 is not connected to port 210.

If double breast pumping is desired, plug member 214 connects tube 212 to a first breastpump assembly and plug member 218 connects tube 216 to a second breastpump assembly. Port 210 does not need to be plugged or capped off since the T-shaped flow passage 302 (see FIG. 5) conveys pressure changes to each tube 212, 216. When single breast pumping is desired, plug connector 218 is engaged with port 210. Alternatively, plug connector 214 can engage with port 210 depending on which breast the mother desires to pump.

Figure 5:
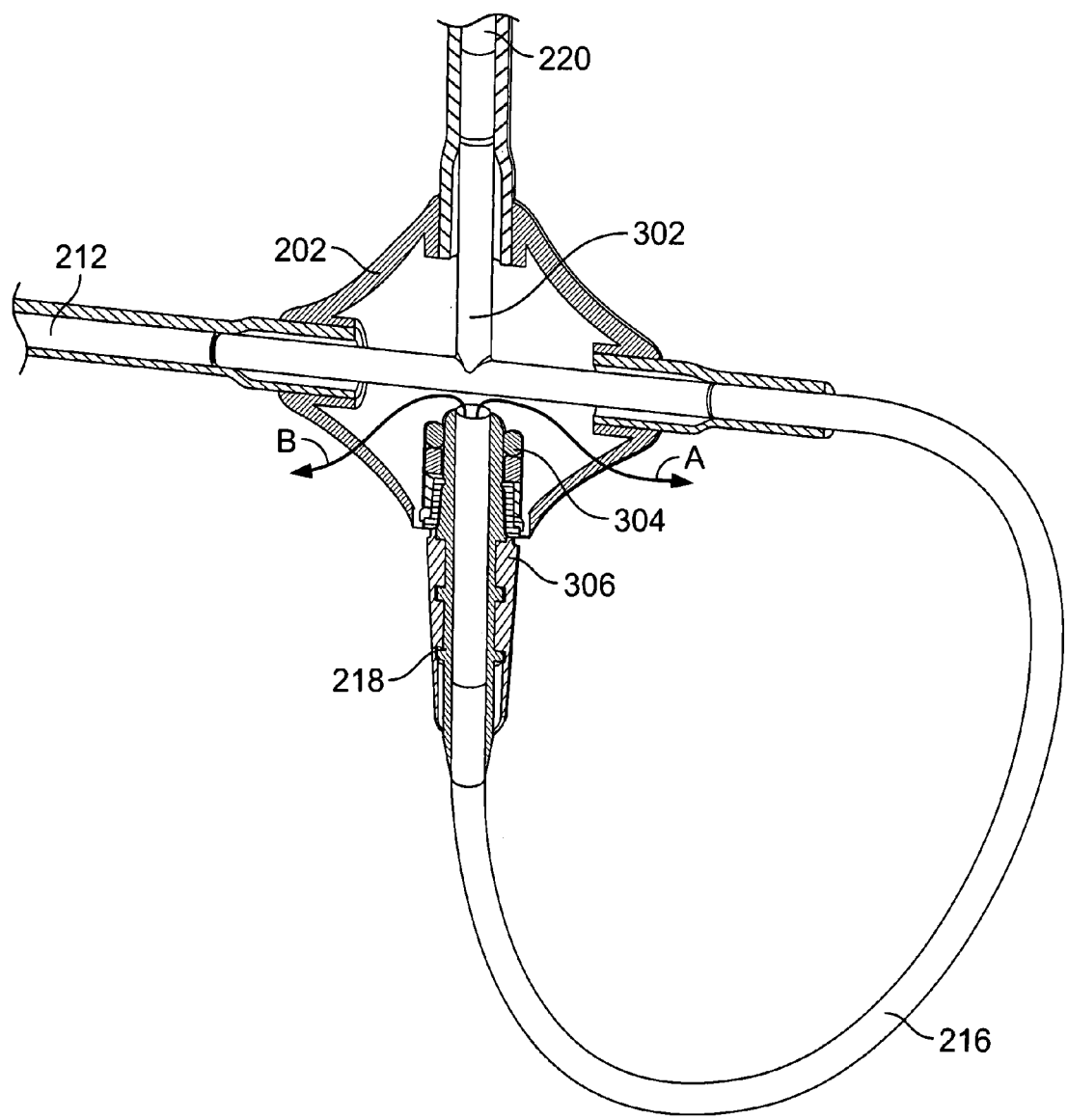
FIG. 5 is a cross-sectional view of the manifold of the connector according to the present invention.

Once plug connector 218 engages with port 210, port 210 provides a predetermined amount of air leakage to simulate the load of the disconnected breastshield, so that the single shield pumping suction level is substantially the same to the double pumping vacuum level. As shown in FIG. 5, two air leakage paths A, B are formed in port 210 such that the disconnected breastshield does not, to a great extent, adversely affect vacuum levels transmitted to the operating breastshield. Path A leaks air past both the sealing ring 304 and latching component 306 whereas path B leaks air past the sealing ring 304 and between the latching component 306 and plug member 218. The leaked air travels into from outside the manifold 202. The leaked air may take any path, including a path through the manifold itself.

It is understood that all shapes and sizes, configurations of the tube connector are contemplated by the invention and are considered various embodiments thereof. It is seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense. It is also to be understood that the following claims are intended to cover all of the generic and specific features of the invention herein described and all statements of the scope of the invention that, as a matter of language, might be said to fall there between.

What is claimed is:

1. A connector comprising,
    a manifold, said manifold including a three-way passageway formed therethrough, said manifold including a first port, second port, third port and fourth port, said first, second and third ports being in fluid communication with said three-way passageway;
    a first tube connected to and in fluid communication with said first port;
    a second tube connected to and in fluid communication with said second port; and
    a third tube connected to and in fluid communication with said third port, wherein said third tube is sized and shaped to be connectable to a vacuum source, and wherein said fourth port is sized and shaped to receive one of said first tube and said second tube and permit a predetermined amount of fluid to pass by way of a leakage path, wherein said leakage path is formed as a part of said manifold in said fourth port.

2. The connector of claim 1, wherein said first, second and third tubes are non-removably connected to said manifold.

3. The connector of claim 1, wherein said fourth port includes an O-ring disposed therein.

4. The connector of claim 1, wherein said three-way passageway is a T-shaped passageway formed in said manifold.

5. The connector of claim 1, wherein said three-way passageway is a Y-shaped passageway formed in said manifold.

6. The connector of claim 1, wherein each of said tubes terminate with a plug member.

7. The connector of claim 6, wherein each of said plug members are adapted to connect with one of said ports to substantially seal said plug members with said ports.

8. The connector of claim 1, wherein said fourth port includes a plug member.

9. The connector of claim 8, wherein one of said first tube and second tube is adapted to connect to said plug member of said fourth port.

10. A connector comprising,
    a manifold, said manifold including a three-way passageway formed therethrough, said manifold including a first port, second port, third port and fourth port, said first, second and third ports being in fluid communication with said three-way passageway;
    a first tube connected to and in fluid communication with said first port and terminating with a first plug member;
    a second tube connected to and in fluid communication with said second port and terminating with a second plug member; and
    a third tube connected to and in fluid communication with said third port and terminating with a third plug member, wherein said third plug member is sized and shaped to be connectable to a vacuum source, and wherein said fourth port is sized and shaped to receive one of said first plug member and said second plug member and permit a predetermined amount of fluid to pass by said plug by way of a leakage path formed as a part of said manifold in said fourth port.

11. The connector of claim 10, wherein said first, second and third tubes are non-removably connected to said manifold.

12. The connector of claim 10, wherein said fourth port includes an O-ring disposed therein.

13. The connector of claim 10, wherein said three-way passageway is a T-shaped passageway formed in said manifold.

14. The connector of claim 10, wherein said three-way passageway is a Y-shaped passageway formed in said manifold.

15. The connector of claim 10, wherein each of said plug members are adapted to connect with one of said ports to substantially seal said plug members with said ports.

* * * * *